United States Patent [19]

Smargiassi et al.

[11] Patent Number: 4,727,871
[45] Date of Patent: Mar. 1, 1988

[54] VENTILATOR EXHALATION SYSTEM

[75] Inventors: Paul R. Smargiassi, Oceanside; Guy Gansel, Santa Ana, both of Calif.

[73] Assignee: Infrasonics, Inc., San Diego, Calif.

[21] Appl. No.: 791,688

[22] Filed: Oct. 28, 1985

[51] Int. Cl.$^4$ .................. A61M 16/00; A62B 7/00
[52] U.S. Cl. ..................... 128/204.17; 128/205.12; 128/205.27
[58] Field of Search ............. 128/203.16, 203.17, 128/203.26, 203.27, 204.17, 204.21, 205.12, 205.15, 205.24, 205.27, 205.28, 205.29, 716, 719, 725, 910; 137/341; 73/198, 199, 200, 201, 863.11, 863.24

[56] References Cited

U.S. PATENT DOCUMENTS

| | | | |
|---|---|---|---|
| 1,808,177 | 6/1931 | Putter | 128/205.28 |
| 2,702,089 | 2/1955 | Engelder | 128/205.27 |
| 3,507,146 | 4/1970 | Webb | 128/719 |
| 3,556,097 | 1/1971 | Wallace | 128/202.23 |
| 3,713,440 | 1/1973 | Nicholes | 128/205.12 |
| 3,789,837 | 2/1974 | Philips et al. | 128/205.15 |
| 3,871,371 | 3/1975 | Weigl | 128/201.17 |
| 3,893,458 | 7/1975 | Fletcher et al. | 128/205.29 |
| 3,968,812 | 7/1976 | Eross | 128/205.12 |
| 4,060,576 | 11/1977 | Grant | 128/203.27 |
| 4,214,147 | 7/1980 | Kraver | 137/341 |
| 4,259,303 | 3/1981 | Nakaji et al. | 128/910 |
| 4,360,018 | 11/1982 | Choksi | 128/205.12 |
| 4,391,271 | 7/1983 | Blanco | 128/205.27 |
| 4,537,748 | 8/1985 | Billiet | 128/205.29 |

Primary Examiner—Kyle L. Howell
Assistant Examiner—Karin M. Reichle
Attorney, Agent, or Firm—Brown, Martin, Haller & Meador

[57] ABSTRACT

An exhalation system for connection in the exhalation path of a ventilator for assisting a patient's breathing includes a heated bacteria filter for heating exhaled gas passing through it to a temperature high enough to substantially avoid condensation in the filter. A connecting passageway on the downstream side of the filter for connection to a monitoring device is also heated along at least part of its length to add additional heat to the gas passing through it so that condensation in the connecting passageway and monitoring device is substantially avoided.

9 Claims, 5 Drawing Figures

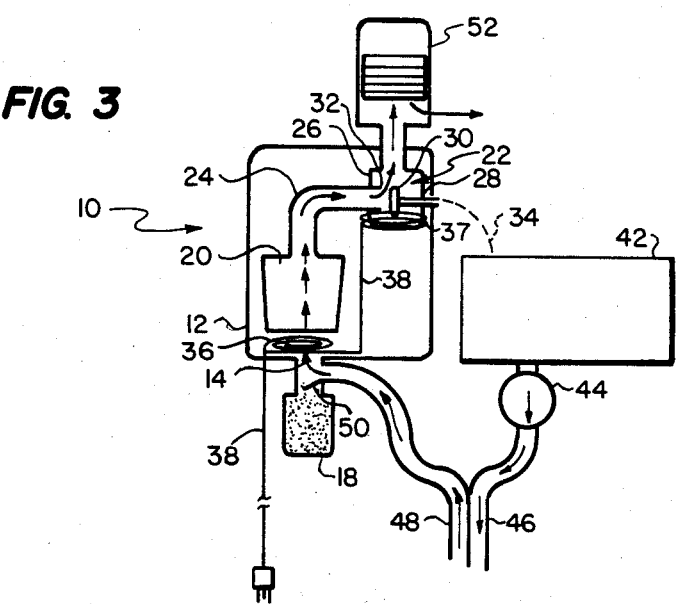
FIG. 3
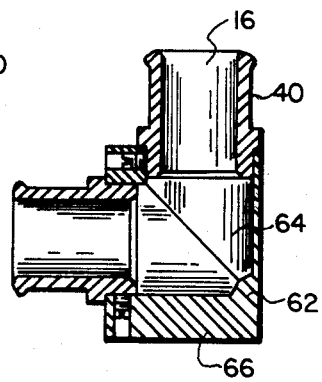
FIG. 5
FIG. 4

VENTILATOR EXHALATION SYSTEM

BACKGROUND OF THE INVENTION

The present invention relates to an exhalation system for use with ventilators, particularly adult volume ventilators used to control and assist a patient's breathing.

Ventilator breathing systems for assisting respiration of patients who are unable to breathe adequately on their own normally include an inhalation hose through which a controlled mixture of gas from the ventilator is inhaled by the patient, and an exhalation assembly through which gas is exhaled. The exhalation assembly normally includes an exhalation valve for shutting off the outlet path while the patient is inhaling, and a flow meter or other monitoring device such as bellows-type spirometer for monitoring the patient's exhaled tidal volume.

One problem in such breathing systems is in keeping the exhalation components clean, dry and sterile. Exhaled air will contain moisture which tends to cool and condense in the exhalation components, adding to the contamination problem.

Another problem is the risk of contamination of the surrounding air by exhalation of bacteria-laden air from an ill patient. The risk of air-borne or contact cross infection is reduced by incorporation of a bacteria filter in the exhalation path, but this adds another component requiring frequent cleaning and sterilization.

In previous ventilator exhalation systems it has been necessary to disassemble, clean and sterilize the exhalation components on a fairly frequent basis. Some of the components, for example bellows-type spirometers, will collect moisture and are extremely difficult to clean and sterilize. When this must be done on a daily basis, or more frequently in some cases, considerable staff time and costs are involved. Additionally, frequent cleaning and sterilization reduces the component lifetime so that they require more frequent replacement, which also adds significantly to the cost.

In some prior systems the bacteria filter has been heated in an attempt to avoid or reduce condensation in this component. Although this can reduce the build-up of contamination in the filter itself, condensation and contamination in the downstream components such as the spirometer are still a problem.

SUMMARY OF THE INVENTION

According to the present invention a ventilator exhalation system is provided for mounting in the flow path of gas exhaled from a patient on a ventilator. The system includes a bacteria filter and a connecting passageway for connecting the downstream side of the filter to a spirometer or other monitoring device or flow sensor. The bacteria filter is heated and the connecting passageway downstream of the bacteria filter is heated either directly or indirectly along at least a part of its length so as to act as a heat exchanger to heat the gas passing through it and to maintain the heated gas at a temperature high enough to substantially avoid condensation in any of the exhalation system components and any components such as monitoring devices downstream of the exhalation system. The gas temperature will normally be at least about 38° centigrade.

The bacteria filter is preferably mounted in an electrically heated well in an outer housing which can be mounted on an existing ventilator. The connecting passageway downstream of the bacteria filter in one embodiment includes an exhalation valve and heated valve seating assembly mounted within the outer housing. In an alternative embodiment, a portion of the connecting passageway itself is heated. The connecting passageway downstream of the valve seat in the first embodiment, and downstream of the heated portion in the second embodiment is of highly thermal conductive material along at least part of it length so as to be heated by contact with the heated valve seating assembly or heated connecting passageway portion and to act as a heat exchanger to maintain gas passing through it at a high enough temperature to substantially avoid condensation, both in the connecting passageway and in any downstream monitoring device such as a spirometer or other flow sensor.

The connecting passageway in a preferred arrangement includes a support tube of relatively thick, highly thermal conductive material projecting out of the housing. A spirometer or other flow measuring device, e.g. a flow sensor, can be mounted on the support tube either directly or with a suitable connecting device. The support tube is long enough to act as a heat exchanger to add heat to gas passing through it and to maintain the gas at a high enough temperature such that it will not condense in any downstream component, such as a spirometer or flow sensor.

Thus, the exhalation system in both embodiments of this invention substantially reduces or prevents condensation in the system components, which therefore require less frequent cleaning and sterilization.

BRIEF DESCRIPTION OF THE DRAWING

The above and other objects and advantages of the present invention will become clear from the following detailed description of some preferred embodiments of the invention, taken in conjunction with the accompanying drawings in which like reference numeral refer to like parts and in which:

FIG. 3 is a schematic view of a complete ventilator assembly showing the inhalation and exhalation paths with the exhalation system of FIGS. 1 and 2 connected in the exhalation path;

FIG. 4 is a side elevational view, partly broken away, of an exhalation system according to a second embodiment of the invention; and FIG. 5 is a vertical cross-section through part of a connecting passageway of the exhalation system of FIG. 4, taken on lines 5—5 of FIG. 4.

DESCRIPTION OF THE PREFERRED EMBODIMENTS

Figure 1:
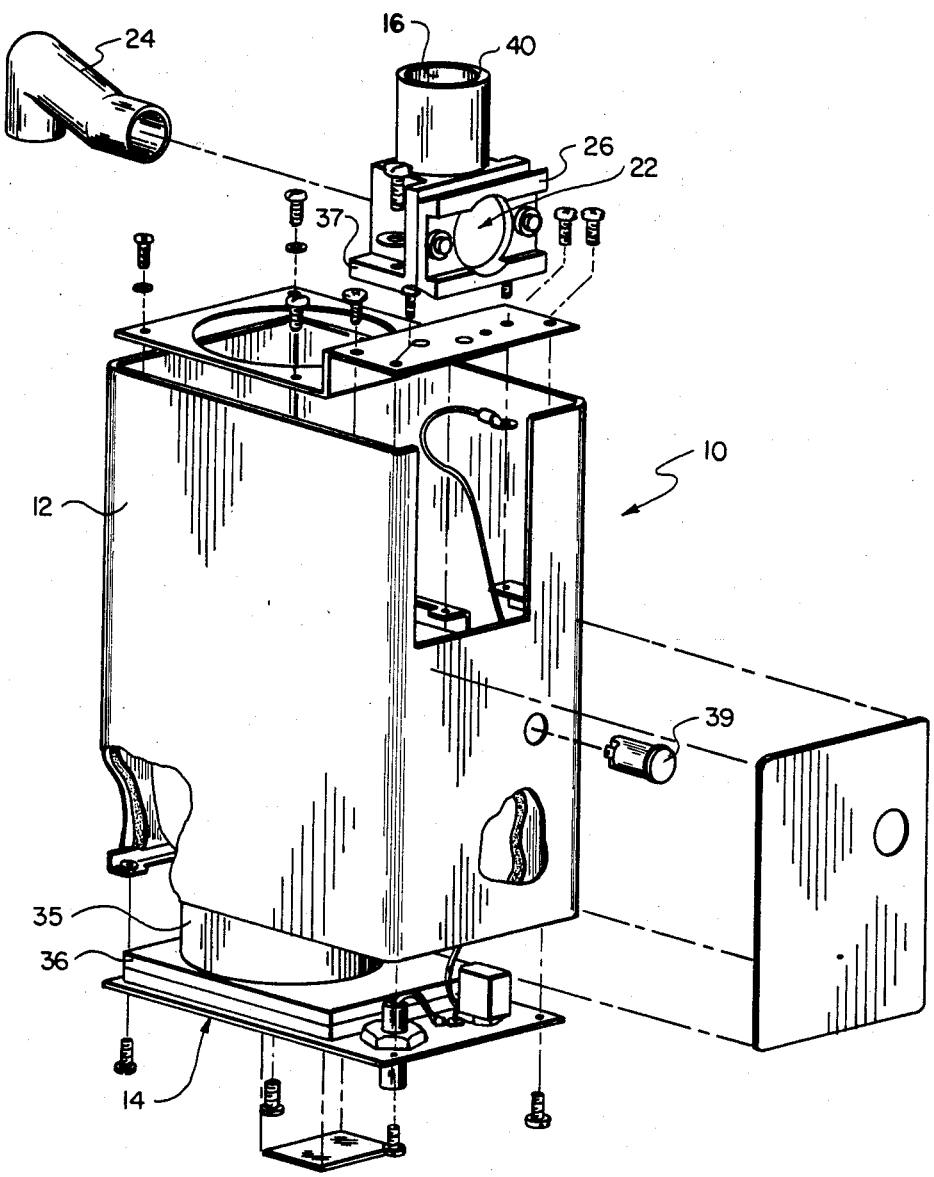
FIG. 1 is a diagramatic exploded perspective view showing an exhalation system according to one embodiment of the invention.
Figure 2:
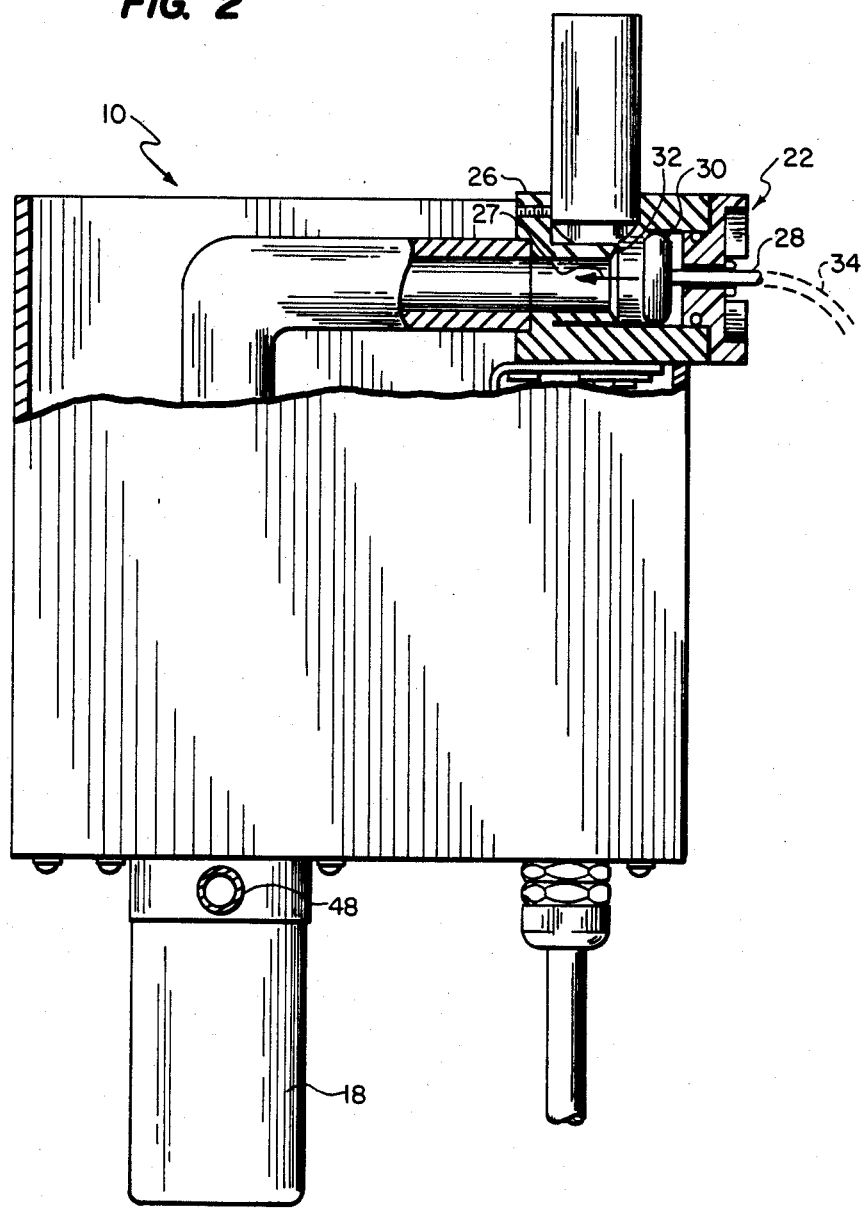
FIG. 2 is a partial vertical cross-sectional view through the exhalation system of FIG. 1 showing the exhalation valve mounting and valve seat.

FIGS. 1 and 2 of the drawings show a first embodiment of an exhalation system according to the invention for connection in the exhalation path of a ventilator for assisting a patient's breathing. FIG. 3 schematically illustrates the connection of such an exhalation system to a ventilator.

As shown in FIGS. 1 and 2, the exhalation system 10 basically comprises an outer housing 12 having an inlet 14 for connecting in the exhalation path of a ventilator and an outlet 16 for connection, for example, to a monitoring device for monitoring a patient's respiration rate. A water trap 18 is mounted below the housing and is connected to inlet 14. The inlet 14 is connected to outlet 16 via a connecting path through the housing 12 including a bacteria filter 20 and an exhalation valve assembly 22. A connecting pipe 24 connects the bacteria filter outlet to the exhalation valve assembly 22.

The exhalation valve assembly 22 basically comprises a valve seat housing 26 having a through bore 27 connecting pipe 24 to outlet 16, and an exhalation valve 28 projecting into the bore with valve head 30 facing a valve seat 32 in the bore 27. The valve is connected to a drive line 34 extending out of the side of the housing for connection to the ventilator in the normal fashion so that the exhalation valve shuts off the exhalation path when the patient is inhaling.

The bacteria filter 20 is mounted in a cylindrical well 35 within the outer housing 12 and may be a standard main flow type bacteria filter commonly used in such applications. The well 35 is of highly thermal conductive material such as aluminum, and is heated by electrical heater element 36 in contact with the base of the well. As can be seen in FIG. 2, the base of the valve seat housing 26 is thickened, and the housing 26 is also of highly thermal conductive material such as aluminum. The valve seat housing 26 is also heated by contact with suitable electrical heating elements 37 such as resistant elements or plates as shown which are in thermal contact with the housing 26. The outer housing 12 is preferably of insulating material. The housing is provided with electrical connecting wires 38 for connecting heating elements 36 and 37 to a suitable source of electricity such as a standard main electricity socket. An indicator light 39 may be provided on the housing to show when the heating elements are on.

The housing outlet comprises a support tube 40 which projects upwardly out of the valve seat housing 26 to project upwardly from the top wall of the outer housing 12. The tube 40 is adapted for connection and support of a respiration monitoring device such as a spirometer 52 as shown in FIG. 3, or a flow tube. The support tube may comprise more than one section, and is removably mounted so that different support tubes may be provided for connecting to different types of flow monitoring devices.

The support tube 40 preferably has relatively thick, highly thermal conductive walls so that it too will become hot by conduction when the valve seat housing is heated. The tube 40 may be of aluminum, for example, and has walls of the order of ¼ inch or more in thickness.

The support tube 40 is preferably relatively long when it is to be connected to a spirometer 52 of the bellows type, as shown in FIG. 3. The spirometer support tube may be of the order of 11½ inches in length. Support tubes for other types of spirometers and flow meter tubes may be of the order of 3 inches in length.

As can be seen in FIG. 1, the entire exhalation system can be taken apart relatively easily for cleaning, sterilization or replacement of the individual components.

The exhalation system is designed for easy connection to any standard ventilation system. This is illustrated schematically in FIG. 3. The exhalation system will be provided with suitable mounting brackets (not shown) to secure it to a ventilator housing.

As indicated in FIG. 3, a ventilator 42 is connected through a humidifier 44 to a connecting hose or passageway 46 defining an inhalation path for a patient. An exhalation path for gas or air exhaled by the patient is provided by connecting hose 48, which is connected by a suitable connector to the inlet 14 of housing 12. As indicated in FIG. 3, the water trap 18 comprises a bottle mounted directly below the inlet 14 to catch water condensed from the exhaled air. The water trap may have an inclined baffle 50 extending across part of its inlet to circulate gas to increase condensation and to provide a surface for condensation of re-evaporated water. The baffle may also promote circular flow to aid in the separation of water droplets. A spirometer 52 is mounted on the support tube 40. The spirometer shown is of the bellows-type. A flow sensor tube may alternatively be mounted on the support tube.

When the exhalation system is connected to a ventilator as shown in FIG. 3, and connecting wires 38 are connected to a suitably electricity supply, the well 35, valve seat housing 26, and support tube 40 will become hot. Thus, when exhaled air or gas flows through the exhalation path of the exhalation system and through the spirometer into the atmosphere, as indicated in FIG. 3, the various heated components in the path act as heat exchangers to heat the exhaled air above normal body temperature. The system is designed to heat the air and maintain it at a high enough temperature to avoid or reduce moisture accumulation as a result of condensation. Thus, the air will be heated and maintained at at temperature above the dew point, or at least 38° C.

The support tube 40 is heated so that air passing through it into the spirometer will be at a high enough temperature so that little or no condensation will occur in the spirometer. This is important since bellows-type spirometers are notoriously difficult to clean and sterilize, and significant moisture accumulation would otherwise be likely to occur in the bellows. In the past frequent cleaning of such spirometers has been necessary.

During inhalation the exhalation valve will move across to the valve seat, closing the exhalation path.

Thus in the exhalation system of this invention not only is condensation in the bacteria filter substantially reduced or avoided, but condensation in all of the downstream components, including respiration monitors such as spirometers or flowmeters, is also avoided or at least substantially reduced. The exhalation system and respiration monitor will therefore require less frequent disassembly for cleaning and sterilization, saving staff time and increasing the useful lifetime of the exhalation components. The exhalation system components, monitoring spirometers, and/or expiratory flow sensors remain clean and dry during relatively long periods of operation.

The exhalation system shown in FIGS. 1 to 3 may be used with existing ventilators such as the Bennett (Registered Trademark) MA-1, MA-2 and MA 2+2, or the Bear (Registered Trademark) 1 or 2, for example.

FIGS. 4 and 5 illustrate an alternative embodiment of the invention, in which the exhalation valve is downstream of the bacteria filter but is located remotely from the heated bacteria filter and connecting passage. This is used with a ventilator incorporating an internal exhalation valve, such as the Siemens 900 B or C.

The exhalation system 60 of FIGS. 4 and 5 is similar to that shown in FIGS. 1 and 3, except that the exhalation valve seat housing is replaced by a connector or joint 62, shown in detail in FIG. 5, having an elbow-shaped or right angled through bore 64 for connecting connecting pipe 24 to housing outlet 16. The connector 62 is of highly thermal conductive material and is heated by a suitable electrical heater 66 in the same way as valve seat housing in the previous embodiment. The other parts of the exhalation system shown in FIGS. 4 and 5 are otherwise equivalent to those of FIGS. 1 to 3 and equivalent reference numerals have been gives for equivalent parts.

As in FIGS. 1 and 3 the exhalation system 60 of FIGS. 4 and 5 acts as a heat exchanger to heat exhaled air passing through the system and maintain it at a temperature above the dew point at least until it exits a downstream exhalation valve and flow monitoring device such as a flow meter or spirometer. This is done by heating both the bacteria filter and the exhalation passageway or path downstream of the bacteria filter.

Thus the exhalation system of this invention essentially isolates a ventilator from the surrounding atmosphere by filtering bacteria from exhaled gas before it enters the atmosphere, and heats the exhaled gas to reduce or eliminate condensation in exhalation components to maintain them cleaner and drier over larger periods of time. By reducing or eliminating condensation in downstream flow meters or respiration monitors, more accurate readings can be obtained. There is no need for any disposable hydrophobic filter on the expirator side of the ventilator breathing circuits, since the exhalation system itself acts as a heat exchanger to reduce or eliminate condensation in exhalation system components.

The exhalation system can be taken apart relatively easily for cleaning and sterilization or replacement of parts such as the bacteria filter, which are removably mounted in the housing for easy disassembly as indicated in FIG. 1. The bacteria filter is sterilized between patients.

The water trap is normally cleaned and sterilized daily. Other components need to be cleaned or sterilized periodically, at a frequency normally no less than once every 6 months.

The exhalation system is separate from the ventilator breathing circuit and can be connected easily to any ventilator. It may be provided with interchangeable support tubes for connection to different types of flow sensors or respiration monitoring devices. The exhalation valve assembly of the first embodiment of the invention described above can be easily removed and replaced with a simple connector as shown in FIGS. 4 and 5 so that the exhalation system can be used with Siemens-type ventilators.

Although the preferred embodiment of the invention has been described above by way of example, it will be understood by those skilled in the field that modifications may be made to the disclosed embodiments which are within the scope of the invention as defined by the appended claims.

We claim:

1. An exhalation system for connection in the exhalation path of a ventilator for use in assisting a patient's breathing, the system comprising:
    a housing having a first end and a second end, an inlet at the first end and an outlet at the second end;
    means for connecting the housing inlet to the exhalation side of the breathing circuit of the ventilator;
    a bacteria filter mounted in the housing and having an inlet and an outlet, means for connecting the filter inlet to the housing inlet;
    first passageway means in the housing for connecting the bacteria filter outlet to the housing outlet;
    second passageway means for connecting the housing outlet to a respiration monitoring device;
    first heating means for heating the bacteria filter to heat gas passing through it to a temperature high enough to substantially avoid condensation; and
    second heating means for heating said first passageway means along at least part of its length to a temperature high enough to maintain gas passing through it at a high enough temperature to substantially avoid condensation in said second passageway means.

2. The system of claim 1, including exhalation valve means in said first passageway means for blocking the first passageway means when the patient is inhaling.

3. The system of claim 2, wherein said second heating means comprises means for heating said first passageway means adjacent said exhalation valve means.

4. The system of claim 1, wherein said second passageway means includes a tube portion of highly thermal conductive material in fluid communication with said bacteria filter, and means for connecting the tube portion to the monitoring device.

5. The system of claim 4, wherein said tube portion has relatively thick walls.

6. The system of claim 5, wherein said walls are approximately ¼ inch thick.

7. The system of claim 1, wherein said first passageway means includes an exhalation valve seat housing having a through bore defining a valve seat, and an exhalation valve in said bore, and means for urging said valve against said valve seat during inhalation phases of the ventilator to close said first passageway means, and said second heating means comprises means for heating said exhalation valve housing.

8. The system of claim 1, wherein said bacteria filter includes a filter housing mounted in the housing and a filter element mounted in said filter housing, said filter housing, exhalation valve seat housing and second passageway means being of highly thermal conductive material and each of said first and second heating means comprising electrical heating means.

9. The system of claim 1, wherein said second heating means comprises means for heating a part of the length of said first passageway means within said housing.

* * * * *